United States Patent [19]
Yamazaki et al.

[11] Patent Number: 5,326,534
[45] Date of Patent: * Jul. 5, 1994

[54] LIQUID COLLECTION TUBE

[75] Inventors: Sakae Yamazaki; Takato Murashita, both of Yamanashi, Japan

[73] Assignee: Terumo Kabushiki Kaisha, Tokyo, Japan

[*] Notice: The portion of the term of this patent subsequent to Oct. 29, 2008 has been disclaimed.

[21] Appl. No.: 927,193

[22] Filed: Aug. 7, 1992

Related U.S. Application Data

[63] Continuation of Ser. No. 449,973, Dec. 12, 1989, abandoned.

[30] Foreign Application Priority Data

Dec. 16, 1988 [JP] Japan .................. 63-317754

[51] Int. Cl.$^5$ ................................................ B01L 3/00
[52] U.S. Cl. ..................................... 422/102; 215/247; 220/229; 604/415
[58] Field of Search ............... 422/102; 215/247, 249, 215/310; 220/229; 604/406, 415

[56] References Cited

U.S. PATENT DOCUMENTS

| | | | |
|---|---|---|---|
| 2,436,291 | 2/1948 | Daniel | 220/229 |
| 3,823,840 | 7/1974 | Zackheim | 215/247 |
| 3,888,377 | 6/1975 | Stadler | 215/249 |
| 4,187,893 | 2/1980 | Bujan | 604/408 |
| 4,266,687 | 5/1981 | Cummings | 215/249 |
| 4,456,138 | 6/1984 | Bercziat | 215/249 |
| 4,512,486 | 4/1985 | Kobayashi et al. | 215/249 |
| 4,598,834 | 7/1986 | Singletary, Jr. | 215/249 |
| 4,657,152 | 4/1987 | Carveth et al. | 215/249 |
| 4,920,976 | 5/1990 | Calzi et al. | 128/764 |
| 5,061,263 | 10/1991 | Yamazaki et al. | 604/403 |

FOREIGN PATENT DOCUMENTS

| | | |
|---|---|---|
| 62185/69 | 1/1970 | Australia . |
| 23933/70 | 12/1970 | Australia . |
| 37895/85 | 8/1975 | Australia . |
| 52621/86 | 7/1986 | Australia . |
| 0059297 | 9/1982 | European Pat. Off. . |
| 0321032 | 6/1989 | European Pat. Off. . |
| 0352322 | 1/1990 | European Pat. Off. . |
| WO88/04154 | 6/1988 | World Int. Prop. O. . |

*Primary Examiner*—James C. Housel
*Assistant Examiner*—Laura E. Collins
*Attorney, Agent, or Firm*—Frishauf, Holtz, Goodman & Woodward

[57] ABSTRACT

A liquid collecting tube for receiving blood or liquid for inspection is disclosed, which has a tubular member and a closure member for closing an open end of the tubular member and made of a material capable of being pierced by a piercing needle. The closing member includes a sealing member for holding the open end of the tubular member sealed when taking out the liquid form the tubular member with a take-out tool and a separable member separablly laminated on the outer side of the sealing member. The separable member is removed so that only the sealing member remains on the tubular member when taking out liquid. The sealing member is film-like and can be readily broken by the take-out tool such as a pipette.

7 Claims, 2 Drawing Sheets

LIQUID COLLECTION TUBE

This application is a continuation of application Ser. No. 07/449,973, filed Dec. 12, 1989 now abandoned.

BACKGROUND OF THE INVENTION

This invention relates to a liquid collecting tube used for clinical test such as blood test.

This type of liquid collecting tube, for instance one for blood test, has a glass or plastic tubular member with a bottom and a closure member closing an open end of the tubular member. The closure member maintains the gas tightness of the tubular member, and also it can be bonded in close contact relation to the tubular member and re-seal a pierced portion after removal of a piercing needle. Typically, a rubber plug type closure member as disclosed in U.S. Pat. No. 4,257,886 is used. With recent automation of test systems, however, difficulties are produced in the handling of the rubber plug type closure member as noted above, and recently a film seal type closure member has been proposed, which is a film including a sealing member capable of re-sealing a potion thereof.

When testing collected blood in the liquid collecting tube, the blood is taken out of the tube. Usually a pipette is used as take-out tool for taking out the blood. When taking out the blood, the pipette should be inserted into the tube. With the tube with a rubber plug type closure member, the closure member is removed from the tube for inserting the pipette. In the case of a film seal type closure member, the pipette is also inserted after peeling off the entire film because a re-sealing member of the closure member can not be pierced by the pipette.

With a blood collecting tube for centrifugal separation of serum or plasma from blood, the film is peeled off after mixing the contained collected blood with a reagent or the like by turning down the tube. Therefore, scattering of attached blood is liable when peeling off the film even if due care is taken, thus giving rise to pollution by the scattered blood and also hazardous contagion of diseases to the operator. Further, since a force in excess of a necessary force is given momentarily to the tube when peeling off the film, not only the attached blood but also the contained blood is liable to be scattered due to vibrations, thus making the problems noted above more significant and also making the handling of the tube more difficult.

SUMMARY OF THE INVENTION

The present invention has been intended in the light of the problems noted above, and its object is to a liquid collecting tube, which permits the take-out operation with a pipette or like take-out tool to be readily performed without need of taking particular care in separating the film when taking out the collected liquid lest the attached liquid should be scattered and also prevents scattering of the collected liquid, thus positively eliminating the environmental pollution and hazardousness to the operator.

To attain the above object of the invention, there is provided a collecting tube having a tubular member with an open end and a closed bottom for receiving a liquid therein and closure means for closing said open end and made of a material capable of being pierced by a piercing needle, said closure means including a film-like sealing member for holding said open end of a said tubular member sealed when taking out the liquid from said tubular member with a take-out tool and a separable member separately laminated on said sealing member on the side thereof opposite said open end of said tubular member.

In this structure, the closure member preferably has a notch formed in a central portion for guiding the take-out tool while the tool is inserted. Further, preferably the separable member includes a gas barrier layer provided on the side laminated to the sealing member and a re-sealing member provided on the opposite side to the laminated side for re-sealing the pierced portion after removal of the piercing needle.

With the liquid collecting tube according to the invention, when the sealing member is peeled off when taking out liquid, only the outer separable member can be readily separated, leaving the film-like sealing member keeping the open end of the tubular member closed. Thus, the film-like sealing member prevents scattering of the liquid contained in the tube. In addition, since the film-like sealing member can be readily broken so that it can be pierced by the take-out tool, the take-out operation can be obtained smoothly via the film-like sealing member.

Further, in a preferred structure according to the invention the closure member is provided with a notch for assisting in insertion of the take-out tool, and the take-out tool can be readily inserted into the tube by piercing the film-like sealing member with the notch as guide.

Further, by forming the separable member such that it consists of a gas barrier layer and a sealing member, the gas tightness of the tube and keeping the tube inside under a reduced pressure can be effectively obtained.

DESCRIPTION OF THE PREFERRED EMBODIMENT

Now, a specific embodiment of the liquid collecting tube according to the invention will be described with reference to the drawings.

Figure 1:
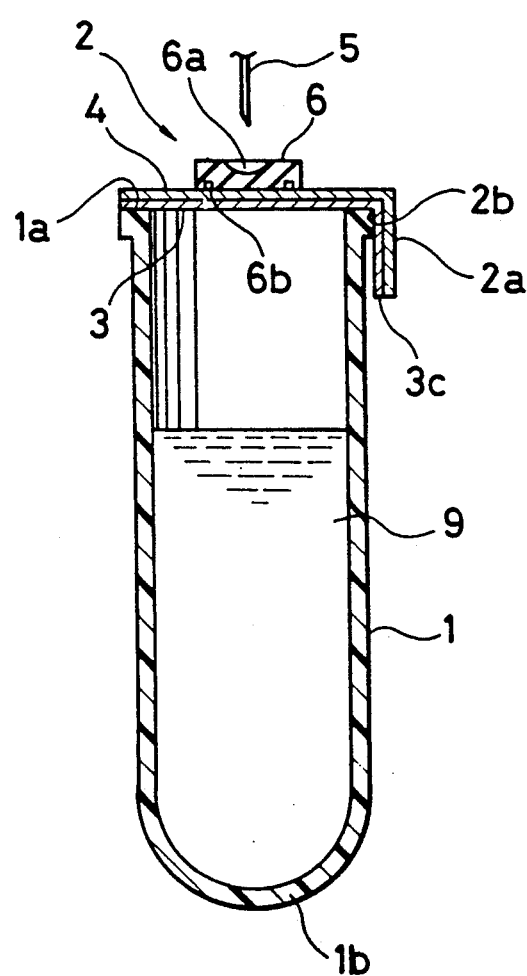
FIG. 1 is a sectional view showing an embodiment of the liquid collecting tube according to the invention.
Figure 2:
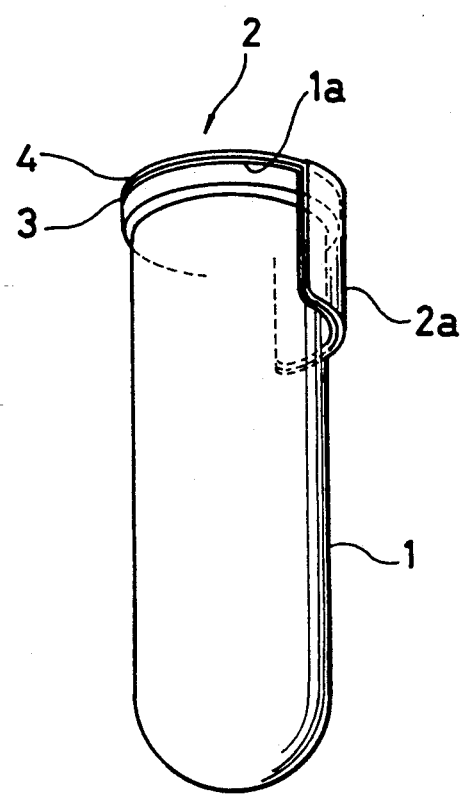
FIG. 2 is a perspective view showing the same liquid collecting tube viewed from the bottom side.

Referring to FIGS. 1 and 2, there is shown a liquid collecting tube. A tubular member 1 of the tube has an open end 1a, which is closed by a closure member 2 of film-seal type as closure means. The closure member 2 has a two-layer structure consisting of an inner film-like sealing member 3 and an outer separable member 4. The film-like sealing member 3 is bonded to the open end 1a of the tubular member 1 with closed bottom 1b. The closure member 2 has an edge extension extending beyond the open end 1a and having an integral tab 2a extending in a bent fashion along the periphery of the tubular member 1. The tubular member 1 has an increased thickness at the open end 1a for provide for an increased bonding area. The separable member 4 is laminated on the outer or upper surface of the sealing member 3 so that the sealing member 3 can remain on the open end 1a in a closing state even after the separable member 4 is separated. In other words, the adhesive strength between the sealing member 3 and separable member 4 is lower than the adhesive strength between the sealing member 3 and open end 1a of the tubular member 1. Further, a disk like re-sealing member 6 is bonded to the center of the outer surface of the separable member 4. The re-sealing member 6 is made of rubber and can seal a pierced portion again after removal of a piercing needle 5. It has a central recess 6a formed on the outer side and an annular groove 6b formed on the lower side and coaxial with the recess 6a.

Figure 3:
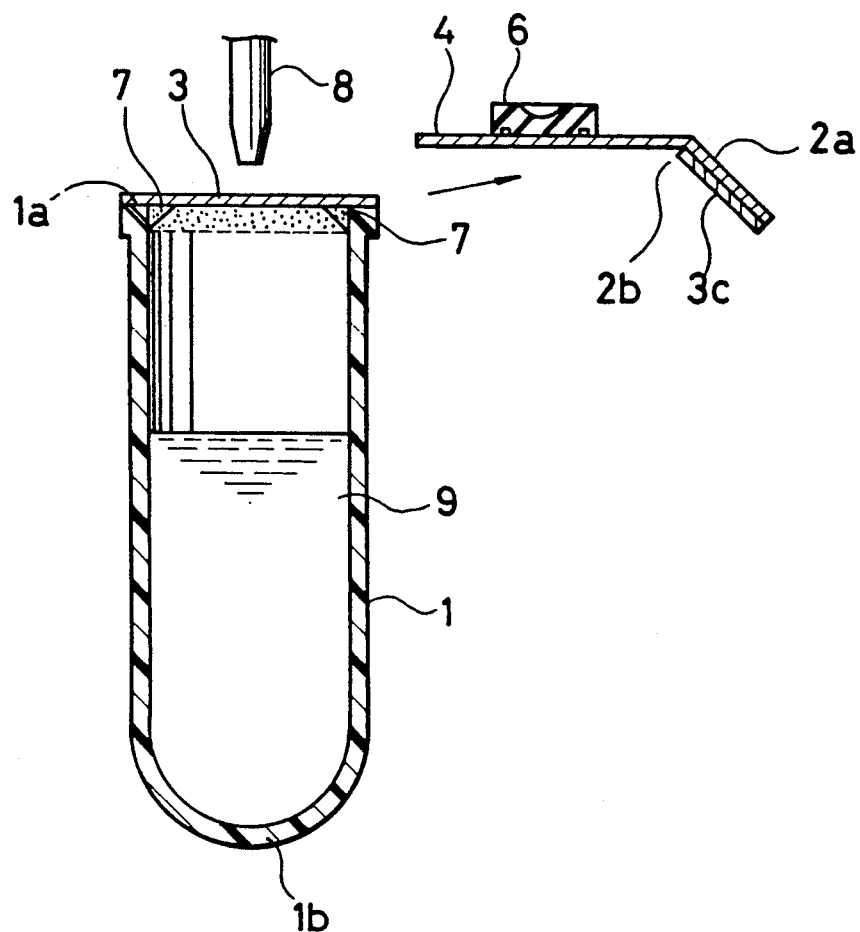
FIG. 3 is a view showing the liquid collecting tube with a separable member of a sealing member shown separated.

With the above construction, when taking out liquid in the liquid collecting tube, the tab 2a is pulled with a hand away from the periphery of the tubular member 1. Since the adhesive strength between the sealing member 3 and separable member 4 is lower than the adhesive strength between the sealing member 3 and open end 1a and also the sealing member 3 has a lower mechanical strength than the adhesive strength between the sealing member 3 and separable member 4, by pulling the tab 2a an extension 3c of the sealing member 3 made overlapped over the tab 2a is broken apart along a bent line 2b of the tab and separated together with the separable member 4 as shown by arrow in FIG. 3. The remaining sealing member 3 on the open end 1a keeps the end 1a closed. Thus, attached liquid 7 attached to the lower or inner surface of the sealing member 3 is never scattered to the outside of the tube.

When collecting blood 9 as liquid to be collected in the liquid collecting tube, the piercing needle 5 is inserted into the tubular member 1 by piercing the re-sealing member 6, separable member 4 and sealing member 3. Thus, the trace of pierce remains as small hole in the sealing member 3 when taking out the collected blood 9. After removal of the separable member 4 with the re-sealing member 6, a pipette 8 or like take-out tool thus can be smoothly inserted into the tubular member 1 without possibility of greatly breaking the sealing member 3 by inserting the pipette 8 or the like with the pierce trace as a guide.

Figure 4:
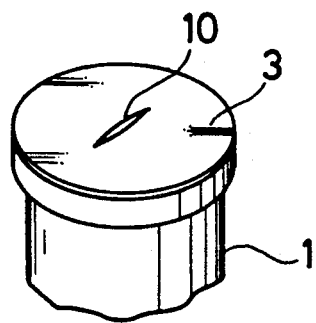
FIG. 4 is a fragmentary perspective view showing the liquid collecting tube viewed from the top thereof, particularly showing a notch formed in a film-like sealing member.

The operation of inserting the pipette 8 or the like may be much facilitated by providing the sealing member 3 at a substantially central position thereof, i.e., the position of the pierce trace of the piercing needle 5, with a lightly greater notch 10, as shown in FIG. 4. The notch 10 is desirably comparatively small lest the contained liquid 9 such as blood should leak to the outside.

The notch 10 need not be provided if the sealing member 3 is made from a material, which is thin and can be readily broken by the take-out tool 8. As an example, the sealing member 3 may have a thickness of 3 to 1,000 $\mu m$, preferably 5 to 20 $\mu m$.

Figure 5:
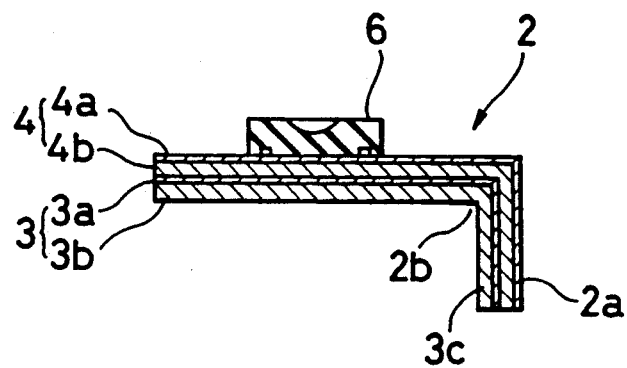
FIG. 5 is an enlarged-scale sectional view showing a sealing member having a multi-layer structure.

While the closure member 2 has a two-layer structure having the sealing member 3 and separable member 4, its more detailed structure is shown in FIG. 5. As is shown, the separable member 4 having a reinforcement layer 4a of polyethylene telephthalate (PET) and a gas barrier layer 4b formed by vacuum deposition of aluminum on the layer 4a, while the sealing member 3 has a layer 3a formed by coating a solution containing polyethylene telephthalate on a gas barrier layer and by causing evaporation of the solvent and an adhesive layer 3b formed by coating denatured polyethylene on the layer 3a. The sealing member 2 may be press stamped together with the tab 2a, and it may be mounted on the tubular member 1 by fusion bonding the adhesive layer 3b to the open end 1a of the tubular member 1.

The reinforcement layer 4a serves to reinforce the gas barrier layer 4b and sealing member 3, and it may be made of nylon, polycarbonate, etc. as well as polyethylene telephthalate. While the gas barrier layer 4b is formed by depositing aluminum, this is by no means limitative; for instance, it is possible to select any material having adequate gas barrier property, which is particularly effective when maintaining the tube inside under a reduced pressure particularly for securing a predetermined quantity of collected liquid, thus permitting predetermined gas tightness to be ensured. The re-sealing member 6 serves to re-seal a portion of the closure member with a pierce trace of the piercing needle for preventing leakage of the collected liquid to the outside of the tube, or more correctly for isolating the collected liquid from the outside.

Further, the layer 3a and adhesive layer 3b noted above are by no means limitative.

While the invention has been described above in conjunction with a preferred embodiment thereof, this embodiment is by no means limitative and can be variously modified without departing from the scope of the invention. For example, while the above embodiment has concerned with the liquid collecting tube for collecting blood 9, the invention is also applicable to a liquid collecting tube for collecting other liquid than blood. Further, while the closure member 2 has a multi-layer structure, this is by no means limitative, and it is only necessary that the sealing member 3 ids film-like so that it can be easily pierced by the take-out tool 8 and can remain on the open end 1a of the tubular member 1 to keep the open end 1a closed.

EXPERIMENT EXAMPLE

The tubular member 1 with bottom as shown in FIG. 1 was formed by injection molding polyester resin (provided by Mitsui PET Co., Ltd. under a trade name "J025/B010" with a weight ratio of 7:3). The inner diameter of the open end 1a of the tubular member 1 was set to 13.4 mm, the taper to 15/1,000, and the thickness to 2.0 mm at the open end 1a (with an outer diameter of 17.3 mm at the open end) and to 1.2 mm for the rest.

As the closure member 2 was used one having the multi-layer structure as shown in FIG. 4 with polyethylene telephthalate used for the reinforcement layer 4a (12 $\mu m$ thickness), aluminum foil for the gas barrier layer 4b (30 $\mu m$ thickness), polyethylene telephthalate as the layer 3a (12 $\mu m$ thickness) and denatured polyester for the adhesive layer 3b (25 $\mu m$ thickness). The re-sealing member 6 used was one having the shape as shown in FIG. 1. It was made of natural rubber. Its diameter was set to 7.0 mm, its thickness to 2.0 mm, the diameter and depth of its recess 6a to 3.0 mm and 0.8 mm, respectively, and the diameter, depth and width of its annular groove 6b to 6.0 mm, 0.2 mm and 0.5 mm, respectively. This re-sealing member 6 is bonded to the center of the outer surface of the separable member 4 by dropping 2 mg of an instant adhesive.

Polypropyrene glycol was coated by dipping on the inner surfaces of the tubular member 1 and sealing member 3. In this tubular member 1 was accommodated 1 mg of a blood solidification promoter containing glass particles (with average size of 2 $\mu m$) and polyvinyl pyrolidon (with weight ratio of glass particles and polyvinyl pyrolidon being 5:1). The tube inside was then held under a reduced pressure (325 mmHg), and then the tube was sterilized by irradiation with 1.0 Mrad of γ-rays, thus, obtaining an experimental liquid collecting tube.

A separate experimental liquid collecting tube was obtained by accommodating 3.0 mm of particles of EDTA-2K in lieu of the glass particles and polyvinyl pyrolidon noted above and holding the tube inside under a reduced pressure of 585 mmHg.

Blood was collected from ten persons using these liquid collecting tubes. More specifically, blood was collected from each person for four tubes, i.e., two liquid collecting tubes containing glass particles and two other tubes containing EDTA-2K, that is, blood for a total of 40 tubes was collected from ten persons. The separable member 4 was peeled off after one hour from the collecting operation. With all the 40 tubes, the sealing layer 5 remained on the tubular member 1, and no scattering of blood was found.

As has been described in the foregoing, with the liquid collecting tube according to the invention by pulling apart the closure member 2 for taking out liquid only the separable member 4 is separated, leaving the film-like sealing member 3, which can be pierced by the take-out tool 8, on the open end 1a of the tubular member 1 keep the open end 1a closed. Thus, the possibility of scattering of attached liquid to the closure member when removing the closure member 2 as in the prior art can be precluded, thus permitting prevention of pollution. Further, the sealing member 3 can be readily pierced by a pipette or like liquid take-out tool, thus permitting smooth take-out operation. It is thus possible to provide a liquid collecting tube, which is simple in construction and can be sued safely.

While the above embodiment dealt with blood as the collected liquid, the invention of course is applicable as well to other liquid than blood, for instance humor.

What is claimed is:

1. A liquid collecting tube comprising:
   a tubular member having an open end and a closed bottom for receiving a liquid therein; and
   closure means for closing said open end of said tubular member without using a separate cap member, said closure means being made of a material capable of being pierced by a piercing needle;
   said closure means including:
      a film sealing member for maintaining said open end of said tubular member sealed when taking out the liquid from said tubular member with a take-out tool which is insertable through said film sealing member, said film sealing member being bonded to and sealing said open end of said tubular member with a first adhesive strength; and
      a separable member separably laminated on said film sealing member on the side thereof opposite said open end of said tubular member, said separable member being bonded to said film sealing member and being separable from said film sealing member prior to insertion of said take-out took into said tubular member through said film sealing member;
      said separable member comprising a gas barrier layer provided on the side of said separable member which is laminated on said film sealing member, and a re-sealing member provided on the side of said separable member opposite to the side thereof which is laminated on said film sealing member, said re-sealing member re-sealing the closure means which is pierced by the piercing needle after removal of the piercing needle from said closure means; and
      said separable member being bonded to said film sealing member with a second adhesive strength which is lower than said first adhesive strength.

2. The liquid collecting tube according to claim 1, wherein said film sealing member has a notch formed in a central portion thereof for guiding insertion of said take-out took being inserted through said film sealing member to take out said liquid from said tubular member.

3. The liquid collecting tube according to claim 1, wherein said closure means includes an integral tab which extends beyond an area of said open end of said tubular member, said tab having a bent portion extending along the outer periphery of said tubular member below said open end of said tubular member, said tab including an extension of said film sealing member, said extension being capable of being broken apart from the rest of said film sealing member when said tab is pulled away from the periphery of said tubular member.

4. The liquid collecting tube according to claim 1, wherein said film sealing member has a thickness of 3 to 1,000 μm.

5. The liquid collecting tube according to claim 4, wherein said film sealing member has a thickness of 5 to 20 μm.

6. The liquid collecting tube according to claim 1, wherein said separable member comprises a reinforcement layer on the side thereof which is laminated on said film sealing member, and said re-sealing member being on said gas barrier layer in a substantially central portion of said separable member.

7. The liquid collecting tube according to claim 6, wherein said re-sealing member comprises a guide area for guiding insertion of said piercing needle therethrough.

* * * * *